(12) United States Patent
Mazlin et al.

(10) Patent No.: US 12,329,455 B2
(45) Date of Patent: Jun. 17, 2025

(54) FULL-FIELD OPTICAL COHERENCE TOMOGRAPHY IMAGING METHOD

(71) Applicants: Paris Sciences et Lettres, Paris (FR); Centre National de la Recherche Scientifique (CNRS), Paris (FR); Ecole Superieure De Physique Et De Chimie Industrielles De La Ville De Paris, Paris (FR)

(72) Inventors: Viacheslav Mazlin, Paris (FR); Pedro Francisco Baracal De Mece, Neuilly-sur-seine (FR); Albert Claude Boccara, Paris (FR)

(73) Assignees: Paris Sciences et Lettres (FR); Centre National de la Recherche Scientifique (CNRS) (FR); Ecole Superieure De Physique Et De Chimie Industrielles De La Ville De Paris (FR)

( * ) Notice: Subject to any disclaimer, the term of this patent is extended or adjusted under 35 U.S.C. 154(b) by 173 days.

(21) Appl. No.: 17/786,714

(22) PCT Filed: Dec. 18, 2020

(86) PCT No.: PCT/EP2020/087156
§ 371 (c)(1),
(2) Date: Jun. 17, 2022

(87) PCT Pub. No.: WO2021/123257
PCT Pub. Date: Jun. 24, 2021

(65) Prior Publication Data
US 2023/0032722 A1 Feb. 2, 2023

(30) Foreign Application Priority Data
Dec. 18, 2019 (EP) .................... 19306683

(51) Int. Cl.
*A61B 3/10* (2006.01)
*A61B 5/00* (2006.01)

(52) U.S. Cl.
CPC ........... *A61B 3/102* (2013.01); *A61B 5/0066* (2013.01)

(58) Field of Classification Search
CPC .. A61B 3/102; A61B 5/0066; G01B 9/02091; G01B 9/02039
See application file for complete search history.

(56) References Cited

U.S. PATENT DOCUMENTS

2003/0072007 A1\* 4/2003 Fercher .............. G01B 9/02091
356/497
2004/0061867 A1 4/2004 Dubois et al.
(Continued)

FOREIGN PATENT DOCUMENTS

| AU | 2015387450 A1 \* | 10/2017 | ........... A61B 3/1005 |
| FR | 2817030 A1 | 5/2002 | |
| WO | WO-2016153571 A1 \* | 9/2016 | ........... A61B 3/1005 |

OTHER PUBLICATIONS

Mazlin, Viacheslav, et al. "In vivo high resolution human corneal imaging using full-field optical coherence tomography." Biomedical optics express 9.2 (2018): 557-568 (Year: 2018).\*
(Continued)

*Primary Examiner* — Tarifur R Chowdhury
*Assistant Examiner* — Roberto Fabian, Jr.
(74) *Attorney, Agent, or Firm* — Lerner David LLP

(57) ABSTRACT

A full-field optical coherence tomography imaging method, FFOCT, using a system comprising an FFOCT device and a sample, the sample comprising a layer of interest to be imaged, the FFOCT device comprising an incoherent light source, an imager, a beam splitter defining a sample arm and a reference arm, the method comprising—generating sample light containing interest light originating from the layer of
(Continued)

interest and reference light traveling from the reference arm, —acquiring an image from reference light and sample light combined in the beam splitter; wherein at least one of the sample arm and the reference arm comprises an optical curvature compensator that modifies a transverse variation distribution of an optical path length to match the transverse variation distributions of the optical path lengths travelled by the reference light and the interest light incident on the imager.

11 Claims, 13 Drawing Sheets

(56) References Cited

U.S. PATENT DOCUMENTS

| | | | | |
|---|---|---|---|---|
| 2005/0134863 | A1* | 6/2005 | De Lega | G01B 9/02039 356/512 |
| 2007/0171366 | A1* | 7/2007 | Su | G01J 1/0414 351/205 |
| 2007/0238955 | A1* | 10/2007 | Tearney | G02B 23/2446 600/407 |
| 2013/0342811 | A1* | 12/2013 | Warm | G01B 9/02091 356/479 |

OTHER PUBLICATIONS

Extended European Search Report for Application No. 19306683.4 dated Jun. 16, 2020. 9 pgs.

International Search Report for PCT/EP2020/087156 mailed Mar. 23, 2021. 3 pgs.

Viacheslav Mazlin et al: "In vivo high resolution human corneal imaging using full-field optical coherence tomography" Biomedical Optics Express, vol. 9, No. 2, Jan. 10, 2018 (Jan. 10, 2018), p. 557, XP055582370. 12 pgs.

Katharine Grieve et al: "Full-field OCT: ex vivo and in vivo biological imaging applications", SPIE—International Society for Optical Engineering. Proceedings, vol. 5690, Apr. 13, 2005 (Apr. 13, 2005), p. 31, XP055700845. 9 pgs.

* cited by examiner

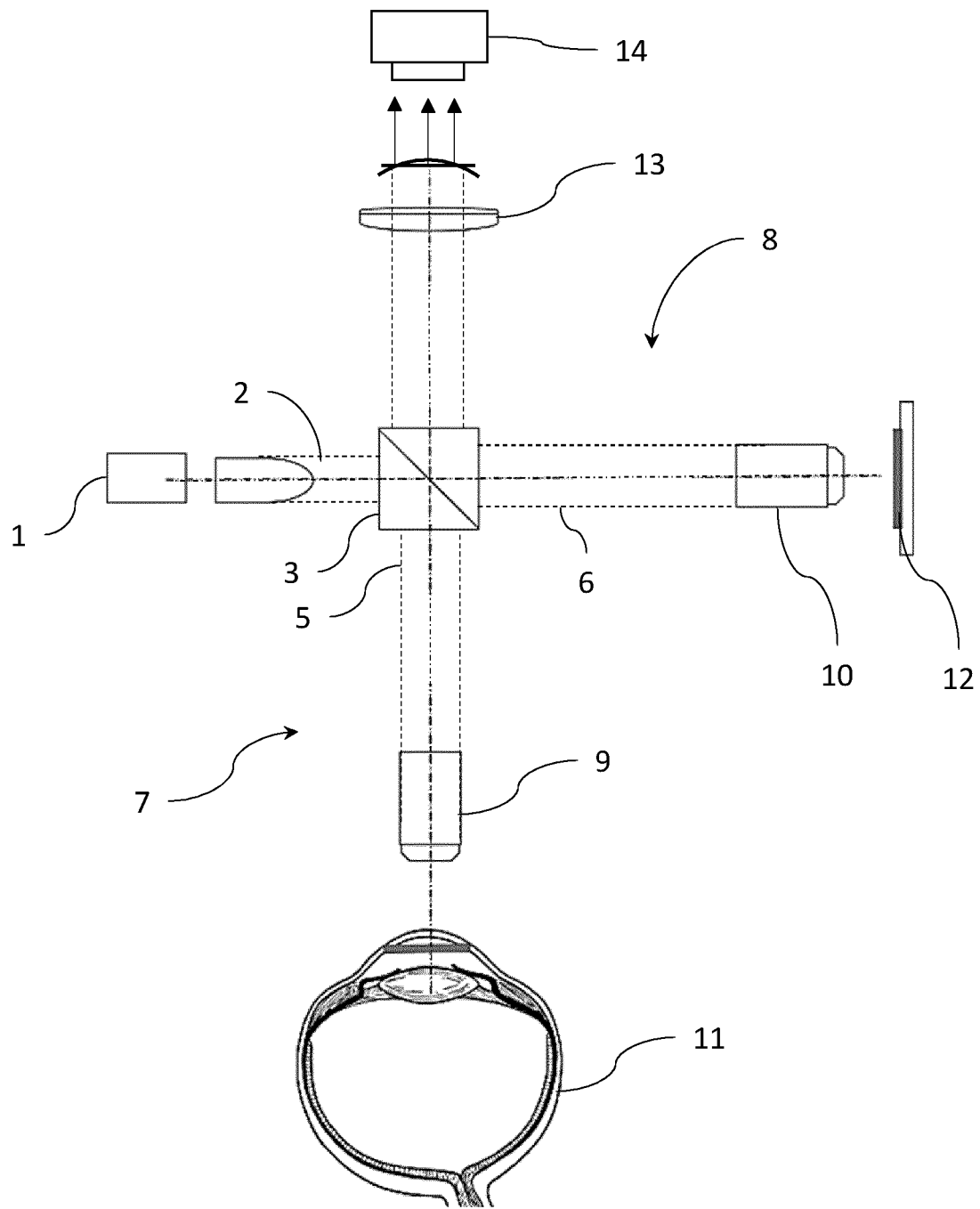

FULL-FIELD OPTICAL COHERENCE TOMOGRAPHY IMAGING METHOD

CROSS-REFERENCE TO RELATED APPLICATIONS

The present application is a national phase entry under 35 U.S.C § 371 of International Application No. PCT/EP2020/087156 filed Dec. 18, 2020, which claims priority from European Application No. 19306683.4 filed Dec. 18, 2019, all of which are hereby incorporated herein by reference.

CONTEXT AND BACKGROUND OF THE INVENTION

The invention relates to the domain of optical coherence tomography (OCT) imaging technique, and more precisely is directed to a new type of Full-field OCT imaging technique. This project has received funding from the European Union's Seventh Framework programme under the HELMHOLTZ grant agreement No 610110.

Full-field OCT (FFOCT) is based on broadband light interference microscopy. Tomographic images are obtained by combination of interferometric images recorded by an imager such as a CCD or CMOS camera. Whereas conventional OCT produces B-mode (axially-oriented) images like ultrasound imaging, full-field OCT acquires tomographic images in the en face (transverse) orientation. More precisely, interferometric images are created by an interferometer, where the path length modulation is usually made by an actuator (usually a piezo element actuated mirror in the reference arm). These images acquired by a CCD camera are combined in post-treatment (or on-line) by the phase shift interferometry method, where several (usually 2 or 4 images) per modulation period are acquired, depending on the algorithm used.

The "en-face" tomographic images are thus produced by a wide-field illumination. This can be obtained by the Linnik configuration of the interferometer, where a microscope objective is used in both arms. Furthermore, while the temporal coherence of the source must remain low as in classical OCT (i.e. a broad spectrum), the spatial coherence must also be low to avoid cross-talks that happen when a spatially coherent light source is used. Full-field OCT is an alternative method to conventional OCT to provide ultrahigh resolution images (~1 µm), using for example a simple halogen lamp instead of a complex ultrashort pulsed laser-based source. Full-field OCT has several specific advantages. Since FFOCT acquires an "en face" image without point-by-point or transverse line by line scanning, FFOCT is immune to transverse scanning artefacts. FFOCT provides higher lateral resolution (of order of 1 µm) than conventional OCT (of order of 10 µm) by using high numerical aperture objectives. This is particularly useful for examining the microscopic cells and tissue structures of the biological samples.

The full-field OCT imaging technique is for example described in the article "Full-field optical coherence tomography" by A. Dubois and C. Boccara, taken from the work "Optical Coherence Tomography—Technology and Applications"—Wolfgang Drexler—James G. Fujimoto—Editors—Springer 2009. This is also disclosed in French patent application FR2817030.

FIG. 1 shows an example of currently used Full-field OCT. A spatially and temporally incoherent light source 1 such as a light-emitting diode (LED) emits a first light beam 2 that is sent to a beam splitter 3. The beam splitter splits the incoming first light beam into a second light beam 5 and a third light beam 6. The second light beam 5 is sent to a sample arm 7 and the third light beam is sent to a reference arm 8.

In a typical FFOCT experiment the setup is usually optically symmetric using the same objective in the two arms of the interferometer. In the depicted example, both arms 7, 8 contains a microscope objective 9, 10 with similar optical properties.

The microscope objective 9 in the sample arm 7 focuses the second light beam 5 on a part of the sample 11 (here a cornea of the human eye), collects the sample light which is reflected from different depths in the sample 11, and transmits the sample light to the beam splitter 3. The microscope objective 10 in the reference arm 8 focuses the third light beam 6 on a flat reference mirror 12, collects the reference light which is reflected from the flat reference mirror 12, and transmits the reference light to the beam splitter 3.

The sample light from different layers of the sample 11 and the reference light from the flat reference mirror 12 recombine at the beam splitter 3 and get focused by a tube lens 13 on a camera 14 that acquires an image. The combination of the sample light and the reference light produces interferences in the camera image plane that are acquired by the camera 14 in a 2D en face image.

However, the interferences are conditioned by a required path correlation between the sample light and the reference light. This path correlation along the image field of view can only be met for a part of the sample light that shows a similar path as the reference light.

The sample light originates from different depths of the sample 11, and therefore is constituted of light components with different path lengths. The different path lengths result in optical path length varying in accordance with the depth where the sample light originates. The reference light has travelled a reference path length, and therefore interferes only with sample light that has travelled a path length equals to the reference path length within the coherence gate thickness, thereby defining in the sample an interfering sample section that corresponds to the origins of the sample light that interferes with the reference light. The coherence gate designates the coincidence path length between the optical path lengths of the reference light and the sample light over which interferences take place.

The reference path length defined by the reference arm 8 thus defines the depth of the interfering sample section. Full-field OCT can therefore be defined as an optical sectioning method, because it is able to extract the sample light originating only from the interfering sample section. The thickness of the interfering sample section is determined by the spectral bandwidth of the light source: the broader the spectrum of the light source, the finer is the interfering sample section.

The camera 14 however collects all the sample light coming from the beam splitter 3, that is to say the interfering light from the interfering sample section, and non-interfering light from the rest of the sample 11 (sections in front or behind the interfering sample section in the optical axis Z). Such an acquired image appears blurred, containing the superimposition of the interfering sample section and of other sections of the sample in the vicinity of the interfering sample section. It is therefore necessary to eliminate the non-interfering light originating from the rest of the sample.

This is usually achieved by acquiring a series of several images (typically 2 to 5 images) of the same sample 11, with a modulated interference phase. The reference mirror 12 is for example translated by using a piezo element that generates an oscillation of the position of the reference mirror 12, hence modulating the reference path length and thus the interference phase. Each acquired image corresponds to a particular interference phase. Post-processing the series of acquired images, non-interfering light can be removed, and the resulting Full-field OCT image reveals only the interfering sample light originating from the particular portion of interest of the sample 11. A 2D final en face image of a portion of interest of the sample 11 is obtained.

Current 2D imaging schemes of FFOCT use a planar reference mirror, which results in the reference beam having a planar path profile. As a consequence, the interfering part of the sample light corresponds to an interfering plane within the sample beam coming from the sample, and originating from a flat slice of the sample. This way of operating is convenient for imaging a flat sample layer of interest, such as a flat surface or a surface that could be flattened, for example skin or an excised tissue.

However, when the sample layer of interest is not flat and cannot be flattened, a major problem arises. This is particularly the case for in vivo eye imaging, wherein the sample cannot be flattened and most of the layers of interest are not flat or appear non-flat when the symmetry of the interferometer is broken between the two arms. For instance, a human cornea is made of a quasi-spherical structure exhibiting large curvatures (about 7 mm radius of curvature), and a FFOCT en face section would display only a small part of the field of view of each corneal layer. FIG. 2a schematically depicts a cross-section view of a cornea, showing a superposition of corneal layers between the anterior cornea (top) and the posterior cornea (bottom). The crosshatched layer is the layer of interest 20 that is to be imaged. The thick line represents the interfering flat plane 21 that is imaged through FFOCT. Due to the curved nature of the layer of interest 20, the interfering flat plane 21 is only partially contained in the layer of interest 20, and corneal layers 22, 23 others than the layer of interest 20 are also intersected by the interfering flat plane 21. FIG. 2b schematically depicts the acquired final image, which corresponds to the intersection between the interfering flat plane 21 and the corneal layers. The layer of interest 20 appears at the center of the final image on a reduced surface area, in the form of a disk. The periphery of the final image shows the other corneal layers 22, 23. The useful field of view of the layer of interest 20 is therefore restricted because of the curved nature of the layer of interest 20. As an example of this configuration, FIG. 2c shows the final FFOCT image of an in vivo corneal layer. The corneal layers are curved and therefore a corneal layer appears as a disk in the center with a good contrast, while other corneal layers appear in the periphery.

FIG. 3a and FIG. 3b show another configuration with similar issues. FIG. 3a schematically depicts a cross-section view of a cornea and the interfering flat plane 31, in a way similar to FIG. 2a. This time, the periphery of the interfering flat plane 31 intersects the layer of interest 30 whereas the center of the interfering flat plane 31 intersects a subjacent corneal layer 32. The outermost periphery of the interfering flat plane 31 intersects another upper corneal layer 33. FIG. 3b schematically depicts the acquired final image, in a way similar to FIG. 2b. This time, the layer of interest 30 does not appear at the center of the final image, but instead as a ring, whereas the subjacent corneal layer 32 appears on the center and the upper corneal layer 33 appears on the outer edge of the image. As an example of this configuration, FIG. 3c shows an example of an imaged sub-basal nerve plexus in the anterior cornea, where the nerve layer appears as a bright ring shaped layer in the final image. FIG. 3d shows an example of an imaged endothelium layer in the posterior cornea, appearing also as a ring in the final image.

The sample can also appear non-flat when the symmetry of the FFOCT device is broken. In retinal imaging for example, the removal of the microscope objective from the sample arm 7 causes a strong asymmetry between the two arms 7, 8 of the FFOCT device. Even if the retina would supposed be flat (in a small field of view it might be the case), the asymmetry would cause a non-flat path profile for the sample light beam.

Previous FFOCT techniques therefore results in an enface image with reduced useful field of view of the layer of interest of the sample.

SUMMARY OF THE INVENTION

The invention proposes a full-field optical coherence tomography imaging method, FFOCT, for acquiring a bidimensional en face FFOCT image of a layer of interest at a depth within a sample, said FFOCT imaging method using a system comprising an FFOCT device and the sample comprising the layer of interest that is to be imaged, the FFOCT device comprising:

a spatially incoherent light source,
an imager,
a beam splitter defining a sample arm and a reference arm, the sample being arranged at an extremity of the sample arm, wherein the method comprises:
simultaneously illuminating the sample arm and the reference arm at an illumination instant with an illuminating light emitted by the incoherent light source to generate sample light travelling from the sample into the extremity of the sample arm along a sample optical path and reference light traveling in the reference arm to the beam splitter along a reference optical path, acquiring a bidimensional en face FFOCT image of the layer of interest with the imager from reference light and sample light combined in the beam splitter;

wherein the sample light contains interest light derived from the illuminating light emitted at the illumination instant and originating from the layer of interest of the sample, said interest light having travelled a first optical path length when entering the sample arm, said first optical path length having a curved profile of transverse variation distribution, wherein reference light incident on the imager has travelled a reference optical path length along the reference optical path, and interest light incident on the imager has travelled a second optical path length, wherein at least one of the sample arm and the reference arm comprises an optical curvature compensator that modifies a transverse variation distribution of an optical path length to compensate the curved profile of transverse variation distribution of the first optical path length, so that the transverse variation distribution of the reference optical path length travelled by the reference light incident on the imager and the transverse variation distribution of the second optical path length travelled by the interest light incident on the imager coincide, resulting in the interest light originating from the layer of interest interfering with the reference light and the imager imaging the layer of interest over a field of view of the imager to form the bidimensional en face FFOCT image acquired by the imager.

Other preferred, although non limitative, aspects of the method of the invention are as follows, isolated or in a technically feasible combination:

a curved profile of the transverse variation distribution of the first optical path length has an absolute radius of curvature comprised between 4 and 50 millimetres;

the transverse variation distribution of the reference optical path length travelled by the reference light incident on the imager and the transverse variation distribution of the second optical path length travelled by the interest light incident on the imager have a difference of absolute radius of curvature below 2 millimetres;

the reference arm comprises an optical curvature compensator that modifies the transverse variation distribution of the reference optical path length travelled by the reference light incident on the imager, and wherein the optical curvature compensator is a curved reflector having a curved reflecting surface, said curved reflector arranged at an end of the reference arm opposed to the beam splitter;

the reflector has a reflectance below 25%;

the curved reflecting surface of reflector is a deformable mirror;

the optical curvature compensator is a plate of material having a refractive index and a thickness in the direction of the reference optical path or the sample optical path;

the optical curvature compensator comprises a pair of prisms, each prism having an inclined surface forming a non-right inclination angle with respect to the optical path, the non-right inclination angles of the pair of prisms being opposite with each other, the prims being movable in translation one with respect to one another;

the optical curvature compensator is a configurable optical curvature compensator, and the FFOCT device comprises a control loop configured to analyse an acquired image and derive a command to change a configuration of an optical curvature compensator, each configuration defining a different modification of the transverse variation distribution of an optical path length;

the method may comprise:
  acquiring a first bidimensional en face FFOCT image of the layer of interest with the imager from reference light and sample light combined in the beam splitter;
  determining whether the curved profile of transverse variation distribution of the first optical path length has been compensated by the optical compensator;
  if it is determined that the curved profile of the transverse variation distribution of the first optical path length was not compensated by the optical compensator, modifying the optical compensator to compensate the curved profile of transverse variation distribution of the first optical path length; and
  acquiring a second bidimensional en face FFOCT image of the layer of interest with the imager from reference light and sample light combined in the beam splitter.

The invention also relates to a full-field optical coherence tomography, FFOCT, device comprising:
a spatially incoherent light source configured to emit an illuminating light at an illumination instant,
an imager configured to acquire a bidimensional en face FFOCT image of a layer of interest,
a beam splitter defining a sample arm and a reference arm, the sample containing said layer of interest at a depth within the sample and being arranged at an extremity of the sample arm,
wherein at least one of the sample arm and the reference arm comprises an optical curvature compensator configured to modify a transverse variation distribution of an optical path length to compensate a curved profile of transverse variation distribution of the first optical path length travelled by an interest light derived from the illuminating light emitted at the illumination instant and originating from the layer of interest of the sample when said interest light enters the sample arm, and the FFOCT device is configured to perform the method of the invention to acquire a bidimensional en face FFOCT image of the layer of interest at a depth within the sample.

BRIEF DESCRIPTION OF THE DRAWINGS

Other aspects, objects and advantages of the present invention will become better apparent upon reading the following detailed description of preferred embodiments thereof, given as non-limiting examples, and made with reference to the appended drawings wherein:

FIG. 1, already discussed, shows an example of a previously used FFOCT system;

DETAILED DESCRIPTION OF THE INVENTION

Figure 2A:
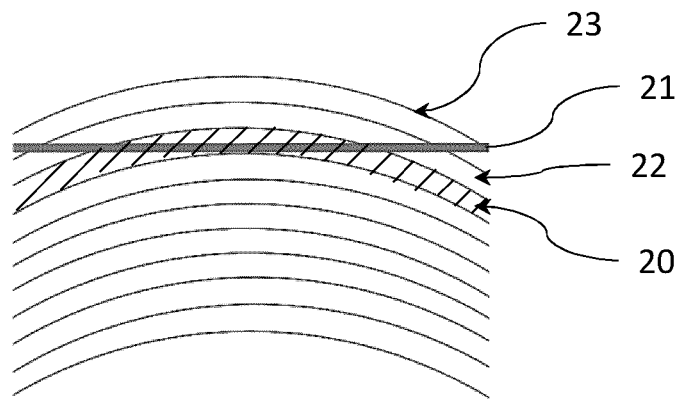
FIGS. 2a, 2b, 2c illustrate how the useful field of view may be reduced when a curved layer of interest is imaged through an interfering flat plane.
Figure 2B:
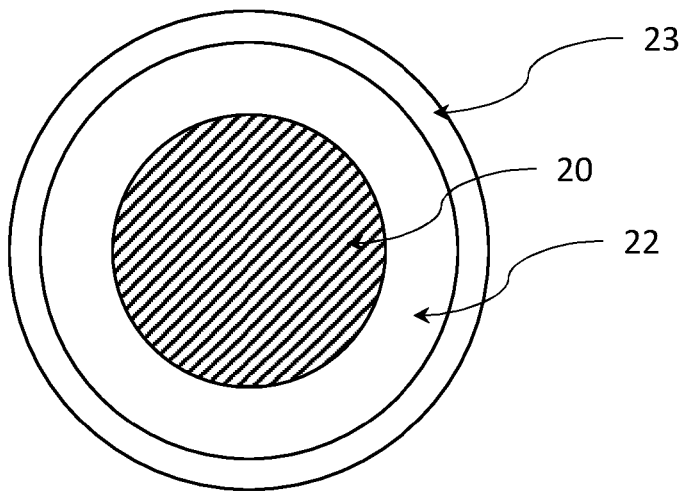

The optical path length is the product of the geometric length of the path followed by light and the mean refractive index of the medium through which it propagates. A light beam does not propagate only along the optical axis, because of its spatial extension in a transverse plane perpendicular to the optical axis, and the optical path length may vary as a function of the considered position on said transverse plane. This is designated as the transverse variation distribution of the optical path length. The transverse variation distribution of the optical path length has a profile defined by the variations of optical path length on the transverse plane.

If the optical path length is the same for all points of the transverse plane, the profile of the optical path length is planar. If the optical path length varies as a function of the considered position on said transverse plane, then the profile of the optical path length is not planar. For example, if peripheral points have a longer or shorter optical path length than points at the center (i.e. on the optical axis), the profile of the optical path length can be defined as curved. The FFOCT system as described in FIG. 1 relies on the difference of the optical path lengths between the reference arm and the sample arm. If the transverse profile of optical path length of the reference arm and the sample arm are the same the transverse profile of the optical path difference appears flat.

In reference to FIGS. 4, 5, 8, and 9 the system comprises an FFOCT device and a sample 111. As in the previously described device, the FFOCT device comprises an incoherent light source 101, an imager 114, a beam splitter 103 defining a sample arm 107 and a reference arm 108. The reference arm 108 extends from the beam splitter 103 to a reflector 112 arranged at an end of the reference arm 108, and defines a reference optical path. The sample 111 is arranged in front of a sample extremity 125 of the sample arm 107, and the sample arm 107 extends from the beam splitter 103 to the sample extremity 125, thereby defining a sample optical path.

The light source 101 is spatially incoherent, i.e. is a source where each point of the source emits waves whose phases are randomly distributed between these points. The light source 101 should have a broad spectrum, typically between 20 nm and 150 nm wide (more preferably between 30 nm and 70 nm wide), comprised between 700 nm and 900 nm, and more preferable around 750 nm and 850 nm. For example, the light source 101 may be a LED or be provided with a filament (as a halogen lamp).

The light source 101 emits an illuminating light at an illumination instant. The illuminating light forms a first light beam 102 that is sent to a beam splitter 103. The beam splitter 103 splits the incoming first light beam 102 of illuminating light into a second light beam 105 and a third light beam 106. The second light beam 105 is sent to the sample arm 107 and the third light beam 106 is sent to the reference arm 108. The sample arm 107 and the reference arm 108 are therefore simultaneously illuminated with the same illumination light.

In the reference arm 108, the light travels along the reference optical path from the beam splitter 103 to the reflector 112 and from the reflector 112 to the beam splitter 103. The second light beam 105 travels along the sample optical path from the beam splitter 103 to the sample extremity of the sample arm 107. The light exits the sample arm 107 and enters the sample 111. The sample light from the second light beam 105 incident on the sample 111 is reflected from different depths in the sample 111 back to the sample extremity of the sample arm 107. The sample light contains light derived from the illuminating light emitted at the illumination instant originating from various depths of the sample 111, and therefore originating from various layers of the sample 111.

The imaging method aims at acquiring an image of a specific layer of interest 115. The layer of interest 115 is defined by a depth within the sample 111 and a shape. Typically, the layer of interest 115 is not flat but rather has a curved surface with respect to the optical axis of the FFOCT device. For example, when the sample 111 is an eye, a layer of interest 115 can have a convex shape viewed from the sample arm 107, for instance for a corneal layer or a crystalline lens, or a concave shape viewed from the sample arm 107, for instance for a retinal layer.

When the interest light originating from the layer of interest 115 of the sample 111 enters the sample arm 107, the light of interest has travelled a first optical path length. The first optical path length is the product of the geometric length of the path followed by light to enter the sample arm 107, and of the mean refractive index of the media through which the light has travelled. If the layer of interest 115 has a curved shape instead of a planar shape, the geometric length transverse profile is changed. In addition to the geometric length variations travelled by the interest light, the transverse variation distribution variation may also result from the refractive index of the media through which the interest light has travelled. A layer of interest 115 lies at a certain depth in the sample 111, which means that the interest light has to travel back and forth through upper layers of the sample 111. If the sample 111 is heterogeneous, those upper layers may have various refractive indexes and may be unevenly distributed. For example, if the layer of interest 115 is a retinal layer, the interest light has to travel through the vitreous humour, the lens, the pupil, and the cornea.

In any case, when entering the sample arm 107, the interest light has travelled a first optical path length with a curved transverse variation distribution. For example, the curved transverse variation distribution of the first optical path length has an absolute radius of curvature comprised between 4 and 50 millimetres. If not compensated, this curved transverse variation distribution will be submitted to an optical sectioning by the reference light that would result in a reduced useful field of view of the layer of interest of the sample, as explained before with reference to FIGS. 2a-c and FIGS. 3a-d.

In order to avoid this problem, the FFOCT device is provided with an optical curvature compensator that modifies a transverse variation distribution of an optical path length. The optical curvature compensator can be arranged in the sample arm 107 or in the reference arm 108. The optical curvature compensator is a curvature compensator configured to compensate the relative curvatures of the profiles of the reference light and of the interest light. Where the optical curvature compensator is arranged in the reference arm 108, the optical curvature compensator modifies the reference optical length across the imaging field of view. Where the optical curvature compensator is arranged in the sample arm 107, the optical curvature compensator modifies the sample optical length across the imaging field of view. The optical curvature compensator is configured so that the reference optical path length travelled by the reference light incident on the imager 114 or the second optical path length travelled by the interest light incident on the imager 114 have the same transverse variation distribution, i.e. the transverse variation distribution of the reference optical path length travelled by the reference light incident on the imager 114 and the transverse variation distribution of the second optical path length travelled by the interest light incident on the imager 114 coincide within temporal coherence length.

Preferably, the profiles of the two respective transverse variation distributions have a difference of absolute radius of curvature below 2 millimetres, and more preferably below 1 mm. When light reaches the imager 114, light waves of the interest light and of the reference light interfere and produce interferences. Interferences occur at each point of the field of view of the imager 114 when the optical path length differences of the waves are superimposed within the temporal coherence length defined by the illuminating light. The proposed optical curvature compensation therefore results in the interest light originating from the layer of interest 115 interfering with the reference light on the image plane of the imager 114, and the imager 114 imaging the layer of interest over a field of view of the imager 114.

Figure 4:
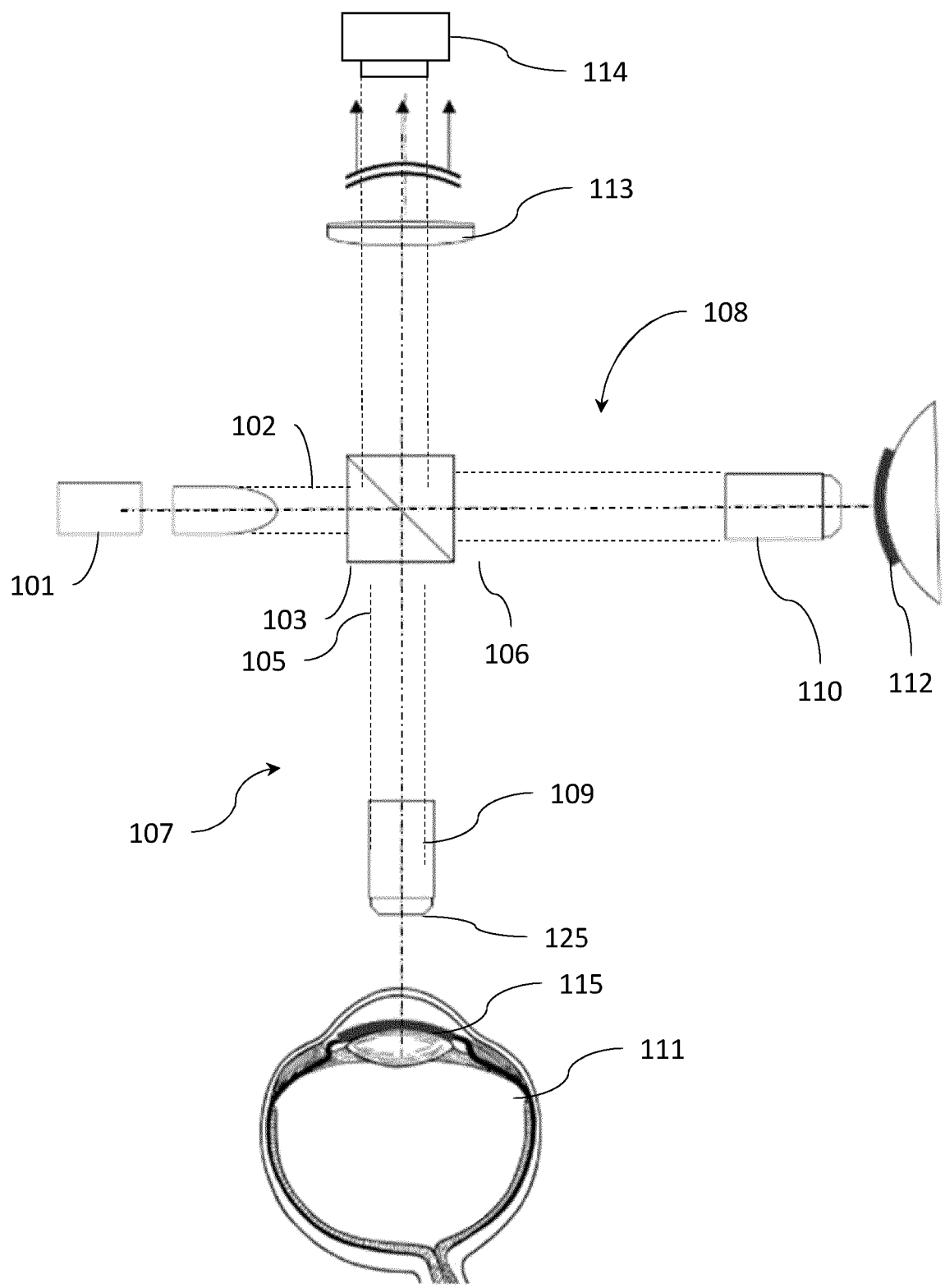
FIGS. 4 and 5 show examples of arrangements for implementing the FFOCT imaging method, wherein the optical curvature compensator is a reflector in the reference arm, according to a possible embodiment of the invention.
Figure 5:
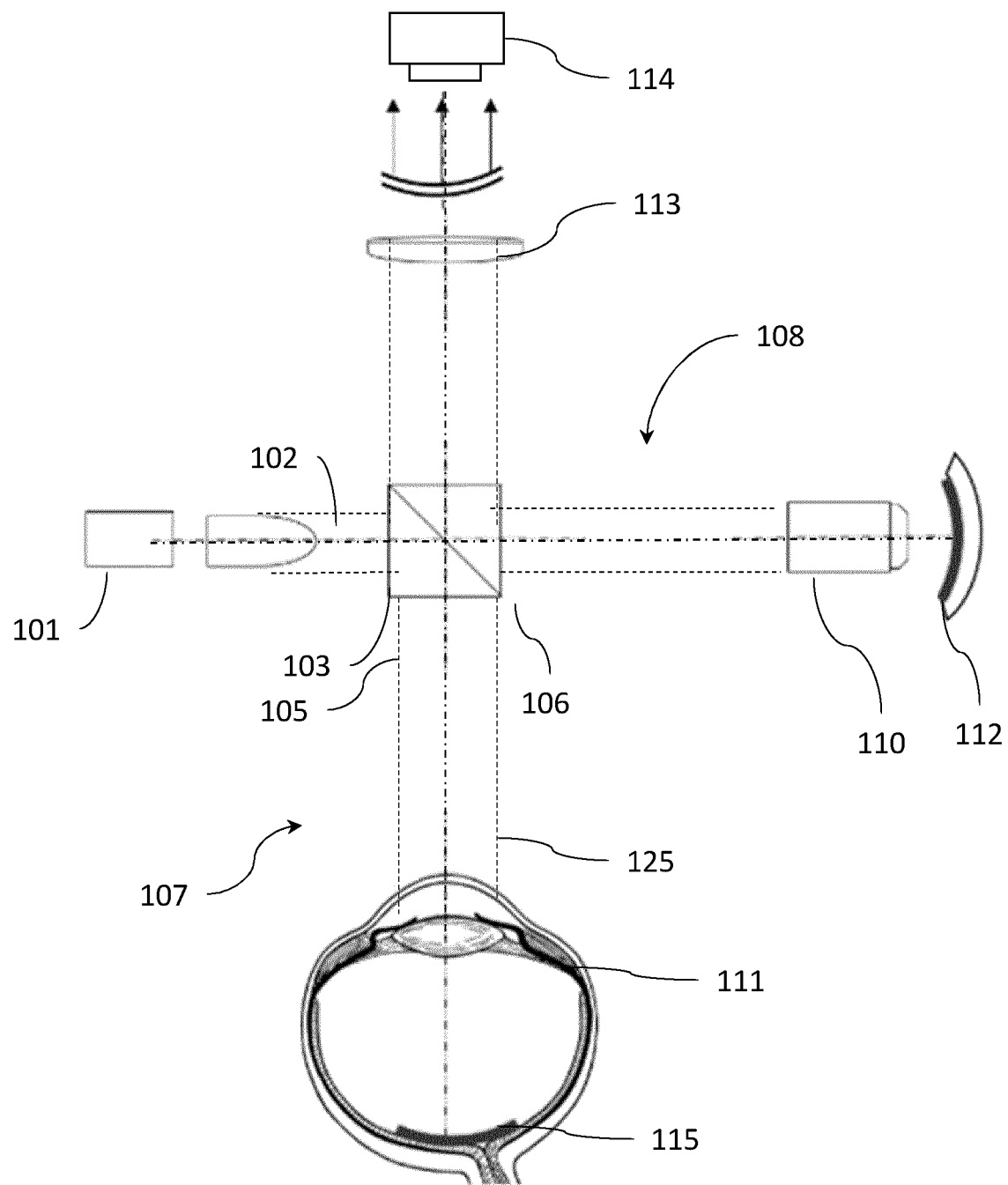

The optical curvature compensator can be a reflector with a curved reflecting surface arranged in the reference arm 108. The optical curvature compensator can therefore be the reflector 112 arranged at an end of the reference arm 108 opposed to the beam splitter 103, if the reflector 112 is curved. FIGS. 4 and 5 show examples of embodiments where a curved reflector is used as an optical curvature compensator. In FIG. 4, the layer of interest 115 is an anterior surface of the ocular lens, which is convex viewed from the FFOCT device. The reflector 112 is also curved in a convex shape viewed from the reference optical path. The curvature of the reflector 112 corresponds to the curvature of the anterior lens, and the radius of curvature is approximately comprised between 9 and 15 mm, and more preferably between 11 and 13 mm. If the layer of interest 115 is the anterior cornea, the radius of curvature of the reflector 112 is comprised between 7 mm and 8 mm. If the layer of interest 115 is the posterior cornea, the radius of curvature of the reflector 112 is comprised between 6 mm and 7 mm. In FIG. 5, the layer of interest 115 is a retinal layer, which is concave viewed from the FFOCT device. The reflector 112 is also curved in a concave shape viewed from the reference optical path. The curvature of the reflector 112 corresponds to the curvature of the retinal layer, and the radius of curvature is approximately comprised between −11 mm and −13 mm. Further, in the retinal imaging configuration of FIG. 5, the microscope objective 109 in the sample arm 7, which was present in the previously described embodiments, is removed. The removal of the microscope objective 109 from the sample arm 7 causes a strong asymmetry between the two arms 7, 8 of the FFOCT device. This asymmetry, combined with the asymmetry caused by the eye medium in front of the retinal layer of interest 115, leads the second optical path length travelled by the interest light incident on the imager 114 to a transverse variation distribution with a curved profile. The curvature of the reflector 112 can therefore be chosen to be higher than the curvature of the retinal layer of interest, to compensate the asymmetry.

It should be noted that the values given here are mere examples and that other values can be used, typically when the sample 111 is not an eye. Even for a human eye, other values can be used to match the curvature of the layer of interest 112. For instance, for a layer of interest 115 constituted by an anterior cornea layer of a patient with keratoconus the radius of curvature of the reflector 112 will be below 6 mm.

The curved shape of the curved reflector 112 causes reflected light to travel an optical path length that varies across the cross-section of the reference optical path, thereby causing a transverse variation distribution of the reference optical path length. By choosing the curvature of the curved reflector 112 to correspond to the curvature of the layer of interest 115, the reference optical path length travelled by the reference light incident on the imager 114 and the second optical path length travelled by the interest light incident on the imager 114 have the same transverse variation distribution. As a result, the optical sectioning perform by the reference light on the sample light selects only the interest light.

The curved reflector 112 can be a mirror, and especially a curved metallic mirror, for example with an aluminium coating as a reflecting surface. However, most mirror have high reflectance, generally higher than 90%. Such a high reflectance is detrimental for FFOCT since image quality is best when the reflectance of the curved reflector 112 matches the reflectance of the sample 111. Since samples 111 and layer of interest 115 generally have a low reflectance, the curved reflector 112 is chosen to have a reflectance below 25%, and preferably below 10%.

The curved reflector 112 is not necessarily a mirror, and can for example be an optical lens. Such an optical lens can be made of glass (for instance RoHS-compliant borosilicate crown glass), fused silica or any other suitable material. An optical glass lens has a naturally low reflectivity, usually below 5%, which corresponds to the reflectivity of many organic sample 111. The optical lens is cheap and can be found with any curvature. For example, an optical lens with a curvature radius of 6.2 mm can be used to match the natural curvature of the posterior human cornea of 6.4 mm. One drawback with optical lens is that reflection might occur not only at the surface of the optical lens, but also from the back surface of the optical lens (secondary reflection). This can be avoided by disposing an absorptive filter (e.g. a glass absorptive filter) at the back of the optical lens, and an immersion liquid between the back of the optical lens and the absorptive filter, the absorption filter and the immersion liquid chosen to have a refractive index close to the refractive index of the optical lens (e.g. 1.518). In this way, light penetrating the optical lens will be absorbed by the absorptive filter without secondary reflection. It is also possible to avoid the unwanted reflection from the back side by choosing for the material of the optical lens a material that absorbs light within the wavelength of the illuminating light (e.g. optical filter glass with selective absorption in certain wavelength ranges).

Figure 6:
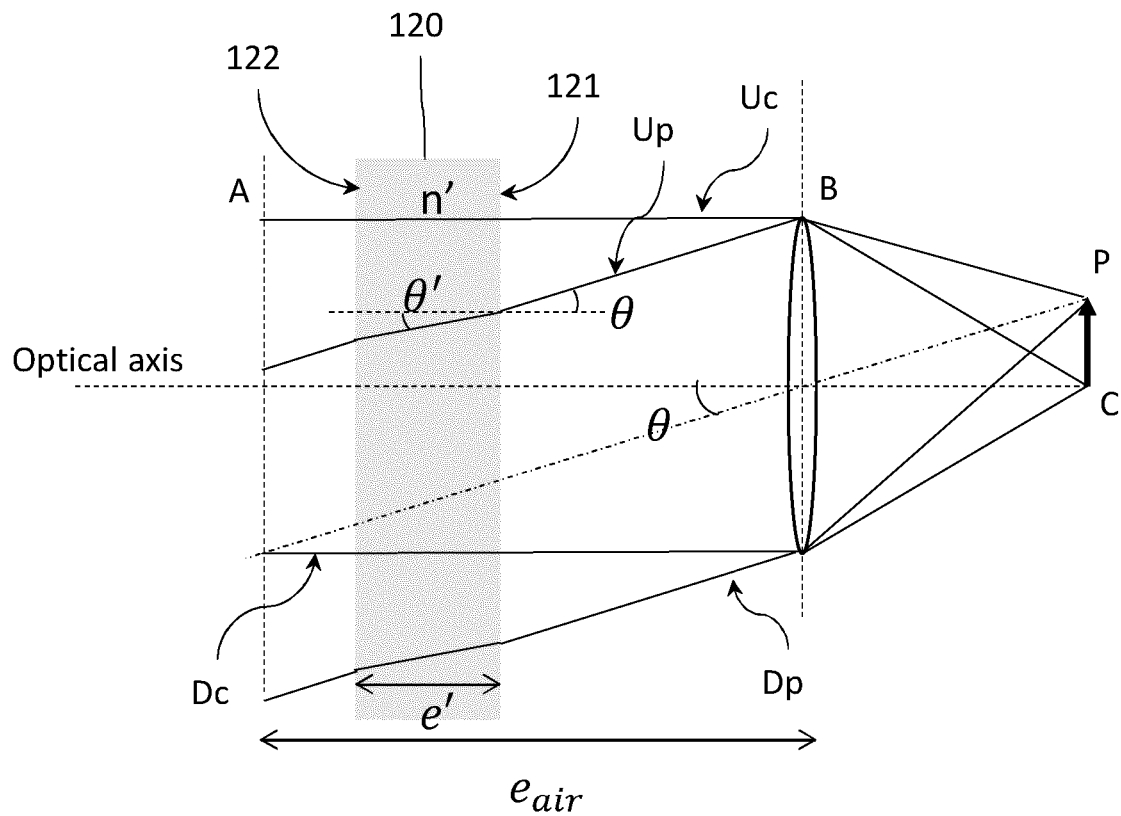
FIG. 6 is a schematic diagram showing how an optical plate modifies the transverse variation distribution profile of an optical path length.

The optical curvature compensator can also be a plate of material having a compensation refractive index and a compensation length along the reference optical path or the sample optical path. Such an optical curvature compensator can thus be arranged in the reference arm 108 or in the sample arm 107. The plate, or optical window, is an optically flat piece of transparent optical material. FIG. 6 is a schematic drawing showing the action of the optical window on the optical path length profile of the light beams. This simplified example deals with light propagation between a proximal arm point A and a distal arm point B, here defined by an optical lens. The proximal arm point A and the distal arm point B are spaced apart a distance $e_{air}$ along the optical axis. The medium between the proximal arm point A and the distal arm point B is assumed to be air (refractive index of 1), except for the optical window 120. The optical window 120 is made of a material with a refractive index n'. The optical window 120 has a thickness e' between two flat surfaces 121, 122 perpendicular with respect to the optical axis.

A central point C of the field of view, on the optical axis, would propagate between arm points A and B in a straight path defined between a straight upper boundary Uc and a straight lower boundary Dc. The central optical path length OPLc would be defined as: $OPLc = e_{air} - e' + e'n'$. A non-central point P of the field of view, is offset from the optical axis so that light coming from said non-central point P would propagate with an angle θ between arm point B and the optical window 120, with an angle θ' inside the optical window, and again with an angle θ between the optical window 120 and the arm point A. In accordance with the Snell-Descartes law, the relationship between θ' and θ is:

$$\theta' = \sin^{-1}\left(\frac{\sin\theta}{n'}\right)$$

The light coming from the non-central point P would propagate in an angled beam defined between an angled upper boundary Up and an angled lower boundary Dp. Such an angled optical path length OPLp would be:

$$OPL_p(\theta) = \frac{e_{air} - e'}{\cos\theta} + \frac{e'n'}{\cos\theta'}$$

It is apparent that the optical window 120 introduces an angle-dependent modification of the optical path length. This means that the resulting transverse variation distribution profile of the optical path length is also angle-dependent, i.e. is curved. By properly choosing the thickness e' and the refractive index n' of the material of the optical window 120, it is possible to adjust the curvature of the transverse variation distribution profile of an optical path length. This is of course a simplified example, and the well-known additional effects must be taken into account by the skilled person. For example, the refractive index of a material usually varies in accordance with the wavelength, and therefore the refractive index n' of the optical window should be noted n'(y). The Sellmeier equation can be used to establish the relationship between refractive index and wavelength for a particular transparent medium.

Figure 7:
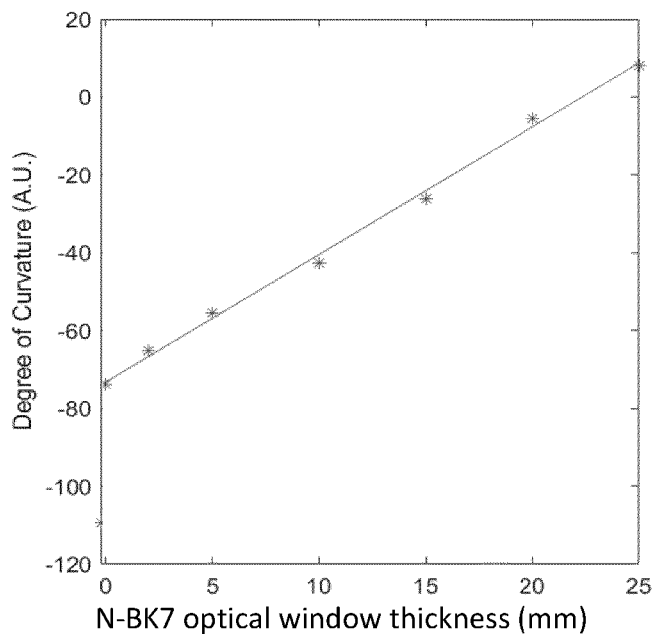
FIG. 7 is a graph showing an example of relationship between a degree of curvature of the transverse variation distribution profile of an optical path length and the thickness of an optical plate.

FIG. 7 is a graph showing an example of how various degrees of curvature (in arbitrary unit) of the transverse variation distribution profile of the optical path length can be obtained with optical window of different thicknesses. The degree of curvature here corresponds to the first coefficient of a parabolic function $f(x) = ax^2 + bx + c$ that models the transverse variation distribution profile of the optical path length. It is sought to compensate a curved transverse variation distribution profile of light coming from a curved corneal layer of a healthy human eye. The optical window is made of borosilicate crown glass, more precisely of N-BK7 glass. Without any optical window (thickness is zero), the degree of curvature is about −73. It takes a 22.3 mm thick optical window to obtain a (second order) planar transverse variation distribution profile, and therefore to compensate the average curvature of a retinal layer of a healthy human eye. It should be noted that light travels twice along the reference arm 108 or the sample arm 107. As a result, travelling light crosses twice the optical plate 120, causing the curvature of the transverse variation distribution profile of the optical path length to be twice affected by the optical plate 120.

Figure 8:
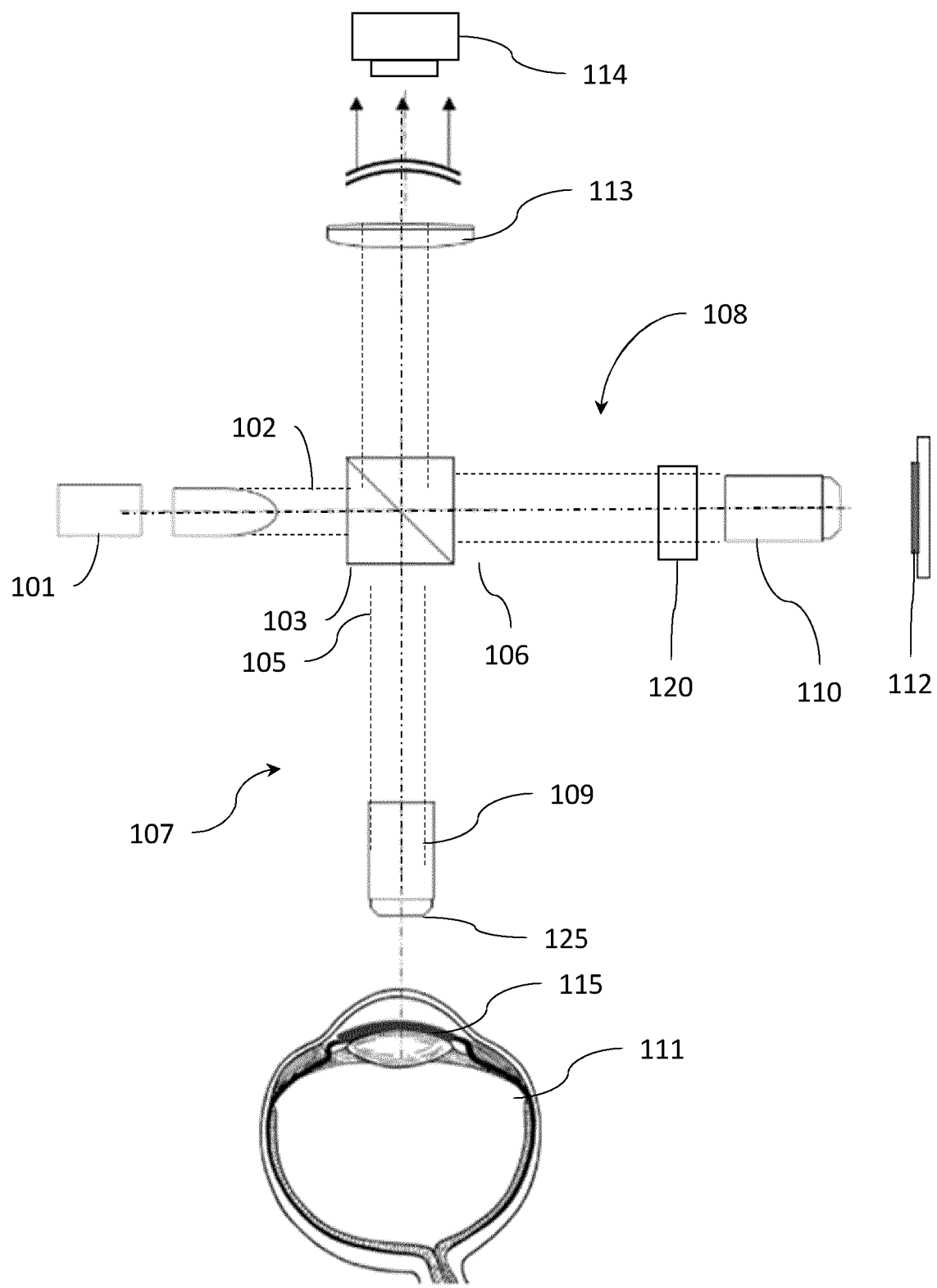
FIGS. 8 and 9 show examples of arrangements of an arrangement for implementing the FFOCT imaging method, wherein the optical curvature compensator is an optical plate arranged either in the reference arm or in the sample arm, according to a possible embodiment of the invention.

FIG. 8 shows an example of an arrangement for implementing the FFOCT imaging method, wherein the optical curvature compensator is an optical plate 120 arranged in the reference arm 108. The optical plate 120 is arranged on the reference optical path between the beam splitter 103 and the reflector 112. The optical plate 120 can be arranged on either side of the sample microscope objective 110, but is preferable disposed between the beam splitter 103 and the sample microscope objective 110. As explained above, the optical plate 120 curves the transverse variation distribution profile travelled by the reference light, so that the reference optical path length travelled by the reference light incident on the imager 114 and the second optical path length travelled by the interest light incident to the imager 114 have a same profile of transverse variation distribution.

The reflector 112 at an end of the reference arm 108 does not need to be curved, and can be flat. It is however possible to combine embodiments, and to provide a curved reflector 112 with an optical plate 120. In this case, the curvature of the profile of the transverse variation distribution of the reference optical path length introduced by the curved reflector 112 is added to the curvature of the profile of the transverse variation distribution of the reference optical path length introduced by the optical plate 120. The features of the curved reflector 112 and of the optical plate 120 are therefore chosen so that the reference optical path length travelled by the reference light incident on the imager 114 and the second optical path length travelled by the interest light incident to the imager 114 have a same profile of transverse variation distribution.

Figure 9:
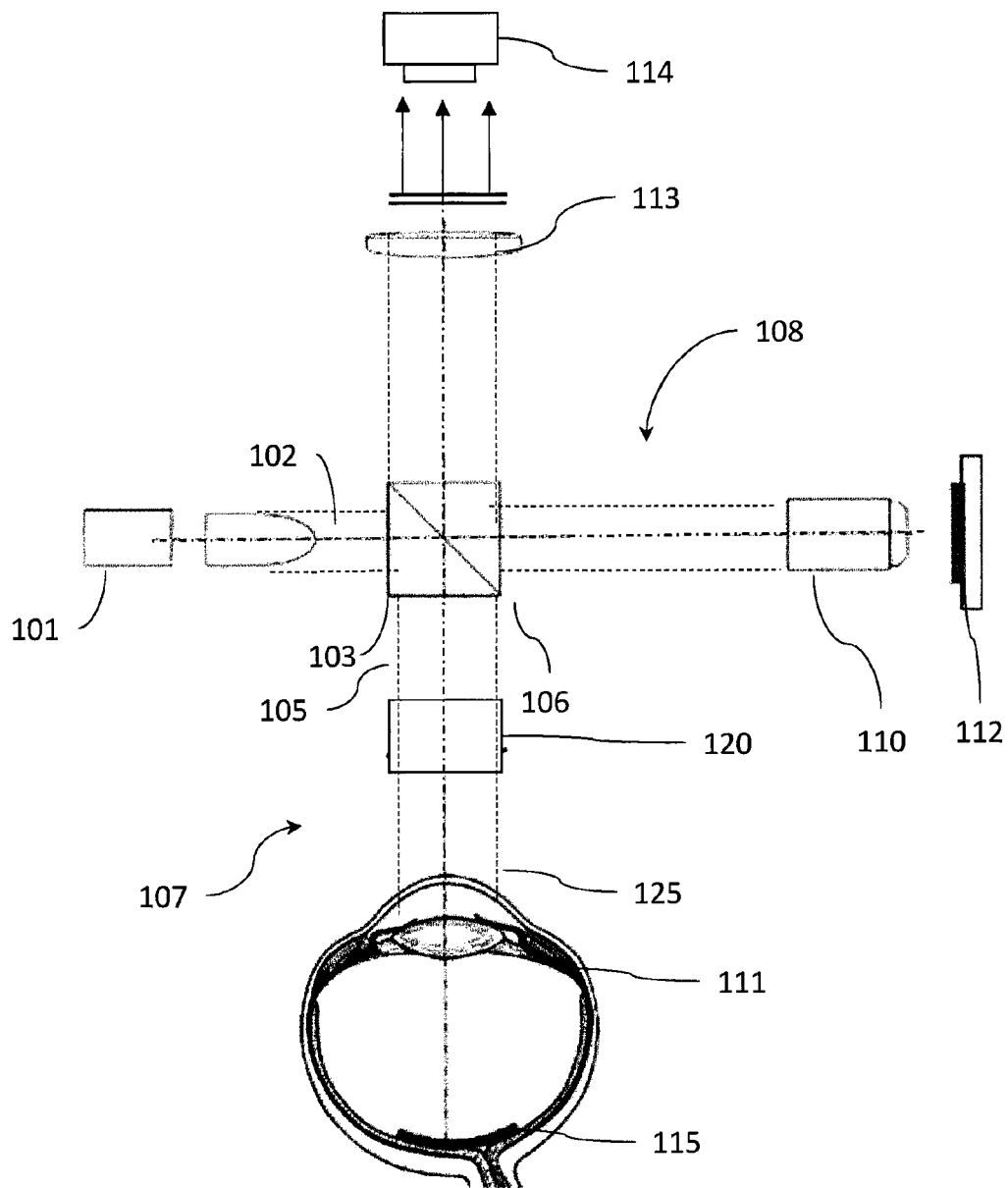

FIG. 9 shows an example of an arrangement for implementing the FFOCT imaging method, wherein the optical curvature compensator is an optical plate 120 arranged in the sample arm 107. Preferably, and as illustrated, the sample arm is devoid of any microscope objective 109. The optical plate 120 is arranged on the sample optical path between the beam splitter 103 and the sample extremity 125 of the sample arm 107. As explained above, the optical plate 120 curves the transverse variation distribution profile travelled by the sample light, so that the sample optical path length travelled by the reference light incident to the imager 114 and the second optical path length travelled by the interest light incident on the imager 114 have a same profile of transverse variation distribution of optical path length.

The features of the optical curvature compensator 112, 120 relating to the modification of the optical path length are chosen to compensate the optical curvature of the layer of interest 115, i.e. the curvature of the profile of the transverse variation distribution of the optical path length travelled by the interest light originating from the layer of interest 115. The optical curvature of the layer of interest 115 can be known, for example when the geometry or optical features of the layer of interest 115 is known, as for a layer of the anterior cornea having a radius of curvature around 7.8 mm. It may however happen that the optical curvature of the layer of interest 115 is not known, or at least not accurately enough. There would be a need to assess the optical curvature of the layer of interest 115.

Figure 10A:
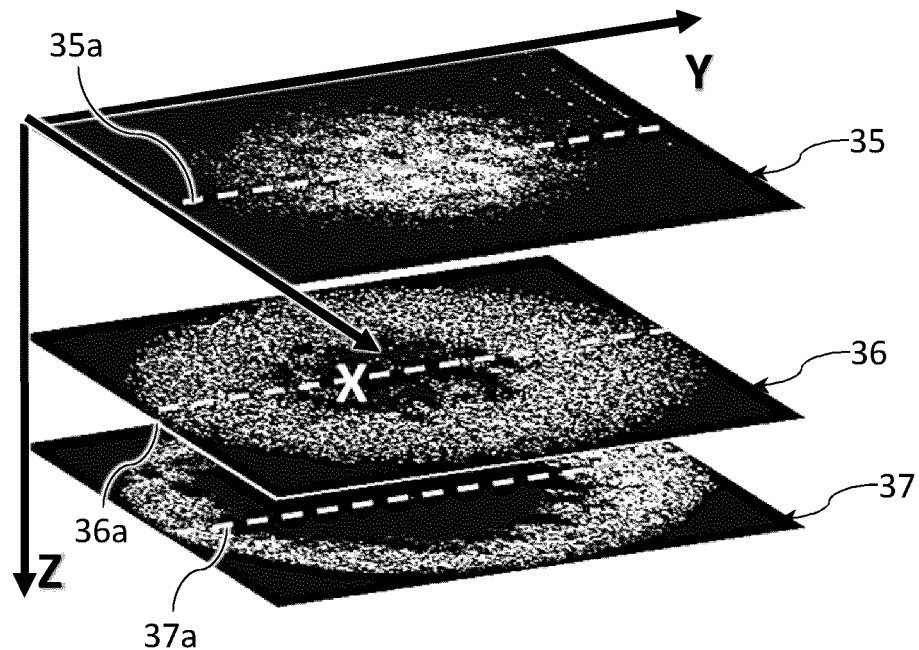
FIGS. 10a and 10b show how to determine a cross-sectional image for assessing the optical curvature of the coherence gate, according to a possible embodiment of the invention.
Figure 10B:
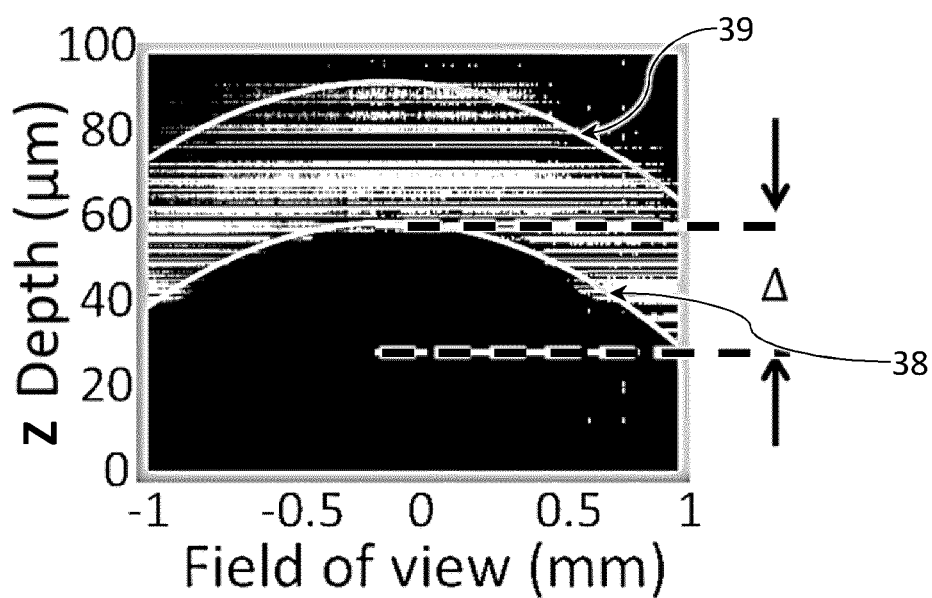

Here is explained a simple way to estimate the optical curvature of the layer of interest 115, allowing the suitable optical curvature compensator to be chosen. While moving the reflector 112 of the reference arm 108 along the optical axis (z axis) at a constant speed, several FFOCT en-face images (in x, y) of the sample 111 are acquired. Various depths of the sample 111 are thus imaged, resulting in a 3D data volume (directions x, y, z), as exemplified in FIG. 10a where three acquired images 35, 36, 37 (extending in x and y) are organized in accordance with the z coordinate of the optical axis assimilated to the depth. A cross-sectional image (in x, z) of the sample 111 can be generated by choosing a same pixel line 35a, 36a, 37a in each image of the acquired image sequence, and concatenating the selection. Such a cross-sectional image is depicted on FIG. 10b.

During the translation of the interference arm 108, the coherence gate kept its curved shape and was translated in z. The resulting cross-sectional image shows the different imaged interfering sample sections (defined by the coherence gate) that corresponds to the origins of the sample light that interferes with the reference light. The lower limit 38 and the upper limit 39 of the imaged area therefore correspond to the profile of the coherence gate. It is possible to measure the difference $\Delta$ in depth (z) between a central point of a limit 38, 39 and a point on the edge of said limit 38, 39. From the difference $\Delta$ and the distance (in y) between the central point and the edge point, the optical curvature of the coherence gate can be derived. Other criteria can be used.

The same approach can be used for assessing whether the optical curvature of the layer of interest 115 has been properly compensated by the optical curvature compensator. If properly compensated, the coherence gate would appear rather flat on a cross-sectional image such as in FIG. 10b. The coherence gate would be considered flat for example if the difference $\Delta$ in depth (z) between a central point of a limit 38, 39 and a point on the edge of said limit 38, 39 is below half the coherence gate thickness, which depends on the bandwidth of the light source 1. For example, if a coherence gate thickness is 8 µm and the difference $\Delta$ is below 4 µm, the curvature of the coherence gate can be considered as compensated.

It is also possible to use the interference fringes on an acquired image to verify the optical curvature compensation performed by the FFOCT device. A test reflector is disposed as a sample in front of the sample arm 107. The test reflector is centred with respect to the optical axis, i.e. the curve of the test reflector is centred. The test reflector has a known curvature that corresponds to the curvature that is wished to be compensated. For example, to verify an optical curvature compensation of a curved layer with a 7.8 mm radius, the test reflector is chosen to have a radius of curvature close to 7.8 mm, and preferably of 7.8 mm. The test reflector can be a plane or curved reflector, a mirror or a dispersion medium which introduces a known curvature to the transverse variation distribution of the optical path length for light propagating through it, possibly associated with a curved reflector.

The test reflector is then illuminated and an image is acquired, in the same way as for a sample 111. From a processing of the acquired image, based on the visible interference fringes density, it is then possible to determine the curvature compensation performed by the optical curvature compensator of the FFOCT device. The fringe density, defined as the maximum number of alternating fringes per millimetres (perpendicularly to the fringes), is directly related to the coincidence between the curvature radius of the test reflector and of the transverse variation distribution of the optical path length.

Figure 11A:
FIGS. 11a-f are examples showing, how the various matching degrees between transverse variation distributions affect the visible interference fringe density in the captured FFOCT image, according to a possible embodiment of the invention.
Figure 11B:
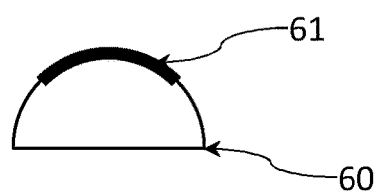
Figure 11C:
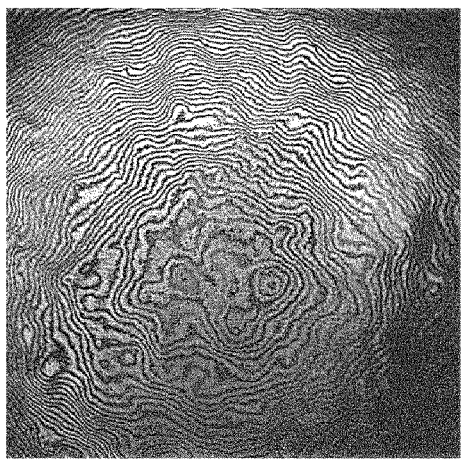
Figure 11D:
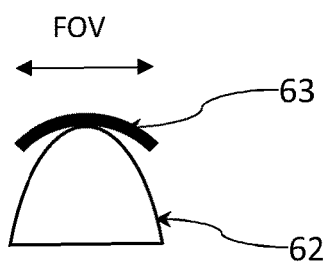
Figure 11E:
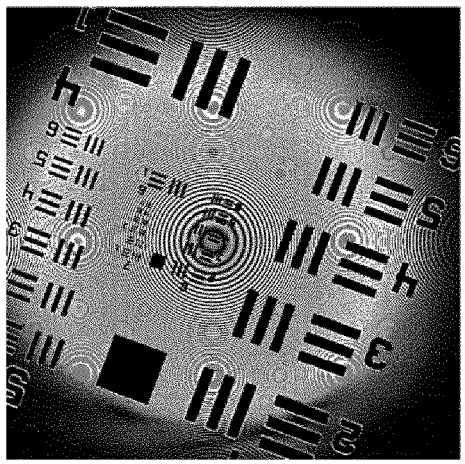
Figure 11F:
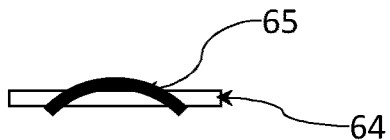

For example, FIG. 11a shows an image corresponding to a first test reflector 60 having a curvature radius of 7.8 mm imaged with an optical curvature compensator configured to compensate a curvature radius of 7.8 mm, resulting in a coherence gate defining an interfering section (corresponding to the origins of the sample light that interferes with the reference light) that has the same curvature as the first test reflector 60, as illustrated in FIG. 11b. In the image of FIG. 11a, the fringes are spaced apart, with a low density. FIG. 11c shows an image corresponding to a second test reflector 62 having a curvature radius of 6.2 mm imaged with an optical curvature compensator configured to compensate a curvature radius of 7.8 mm, resulting in a coherence gate defining an interfering section 63 (corresponding to the origins of the sample light that interferes with the reference light) that has a curvature approaching the second test reflector 62 but not completely the same, as illustrated in FIG. 11d. In the image of FIG. 11c, the fringes are closer than on FIG. 11a, with a higher density. FIG. 11e shows an image corresponding to a third test reflector 65 which is flat (infinite radius of curvature) and is imaged with an optical curvature compensator configured to compensate a curvature radius of 7.8 mm, resulting in a curved coherence gate defining a curved interfering section 64, as illustrated in FIG. 11f. In the image of FIG. 11e, the fringes are very close, much more than on FIG. 11a or 11c, with a very high fringe density.

This is because the fringe density is connected with the optical path difference between the test reflector's surface and the interfering section defined by the coherence gate of the FFOCT device. An interference fringe appears each time the optical path difference reaches the illuminating light's wavelength (850 nm in the examples). That is why the fringe density can be used to assess whether the transverse variation distribution of the reference optical path length travelled by the reference light and of the second optical path length travelled by the interest light coincide. Due to the curved nature of the coherence gate, the optical path differences are higher on the edge of the field of view (FOV) (where the optical path difference is higher) than in the centre of the FOV (where the optical path difference is lower), as seen from FIGS. 11b, 11d, 11f. That explains the concentric aspect of the interference fringes. The maximum density is thus usually found at the edge of the image, that correspond to the edge of the FOV.

A simple criterion on fringe density can be set to assess whether the profiles of the two respective transverse variation distributions have a difference of absolute radius of curvature below 2 millimetres. For an illuminating light at 850 nm and for a FOV of 1.3 mm, the optical curvature of the test reflector is to be considered compensated when the maximum fringe density is below 60 fringes/mm, and preferably below 50 fringes/mm. It shall be noted that the densities are expressed in accordance with the imaged object's field of view, i.e. by taking the magnification into account. In the illustrated examples, the maximum fringe density in the image of FIG. 11a is below 15 fringes/mm, which denotes a good coincidence between the transverse variation distributions, i.e. between the profile of the test reflector and the coherence gate, the maximum fringe density in the image of FIG. 11c is below 50 fringes/mm, which denotes an acceptable coincidence between the transverse variation distributions, whereas the maximum fringe density in the image of FIG. 11e is above 100 fringes/mm, which denotes a lack of coincidence between the transverse variation distributions.

As a result, through a simple measurement involving a test reflector with a known curvature, it is possible to determine whether the optical curvature compensation matches said known curvature.

The optical curvature compensator can be invariant, meaning that the modification of the transverse variation distribution profile of the optical path length caused by the optical curvature compensator is always the same. For example, the modification caused by a curved reflector 112 depends on the curvature of the curved reflector 112, and the modification caused by an optical plate 120 depends on the thickness and refractive index of said optical plate 120. As a result, such an invariant optical curvature compensator can only compensate curvatures of the transverse variation distribution profiles within a limited range. This can be problematic since the curvature of the layer of interest 115 may be only inaccurately known. For example, in clinical applications, patients may present a significant variety of eye length, which would affect the choice of the suitable optical window or curved mirror. As discussed above, the radius of curvature of the reflector 112 will be below 6 mm for an anterior cornea layer of a patient with keratoconus, compared to roughly 7.8 mm for a healthy anterior cornea layer.

One solution is to use changeable optical curvature compensators to suit a wide variety of layer of interest possible curvatures. This could however result in a lengthy process based on trial and error, requiring a number of different optical curvature compensators. It is however possible to make easier the change of optical curvature compensators, for example with an optics wheel, which can be motorized with a stepper motor.

Another solution is to provide a configurable optical curvature compensator. The configurable optical curvature compensator can be a deformable mirror, whose reflecting surface can be deformed. The deformable mirror could be shaped in order to match different kind of surfaces, not only curved surface. For example, the deformable mirror can be based on continuous reflective surface motioned by magnetic actuators.

Figure 12A:
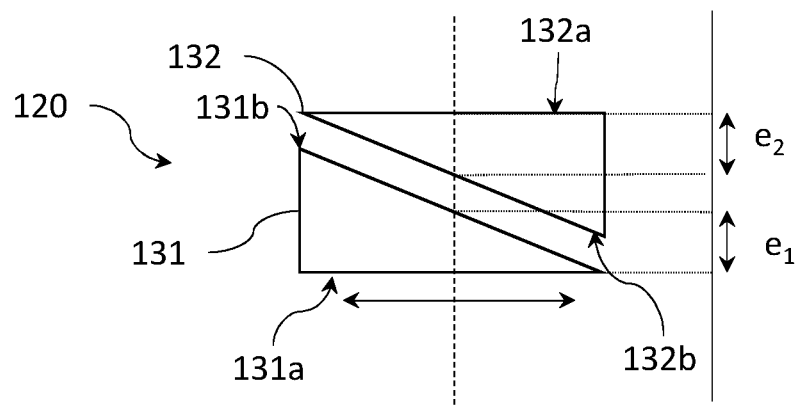
FIGS. 12a and 12b show a configurable optical curvature compensator constituted of a pair of prisms in two different configurations that result in two difference transverse variation distribution profile of an optical path length, according to a possible embodiment of the invention.
Figure 12B:
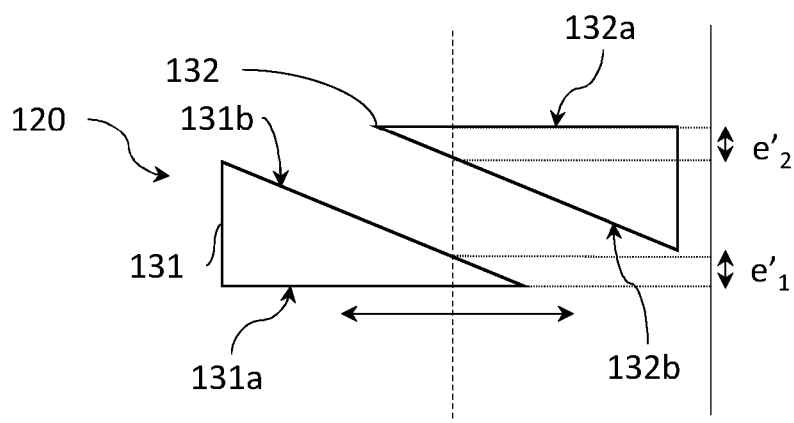

The configurable optical curvature compensator can also be a pair of prisms, as illustrated in FIGS. 12a and 12b. The pair of prisms constitutes an assembly that appears as an optical plate for travelling light. In fact, the pair of prisms is basically an optical plate sectioned in two parts. The two prisms are preferably made of the same material, and preferably have the same shape. There is a first prism 131 and a second prism 132. Each prism 131, 132 has a flat face 131a, 132a that is perpendicular to the optical axis. The two flat faces 131a, 132a constitute the outer faces of the optical curvature compensator. Each prism 131, 132 has an inclined face 131b, 132b forming a non-right inclination angle with respect to the optical axis. The two inclined faces 131b, 132b are opposite to each other and therefore face each other. The two inclined faces 131b, 132b have a complementary inclination. Light travelling through the optical curvature compensator would for example go through the flat face 131a of the first prism 131, the inclined face 131b of the first prism 131, the flat face 132a of the second prism 132, and the inclined face 132b of the second prism 132. In the configuration of FIG. 12a, such light would have travelled through a first thickness e1 of material of the first prism 131 and a second thickness e2 of material of the second prism 132. The pair of prisms is therefore equivalent to an optical plate with a thickness of e1+e2.

The prims 131, 132 are however movable in translation one with respect to one another. More precisely, at least one prism 131, 132, preferably both of them, is moveable perpendicularly to the optical axis. The translation can be motorized. As a result of such a transverse translation, the material thickness crossed by the travelling light is modified. FIG. 12b shows the result of a translation of both prims 131 132 in opposite directions, both transverse with respect to the optical axis. Due to the inclined faces 131b, 132b of the two prisms, the translation results in a modification of the travelled thickness, and more precisely in a reduction for the example depicted in FIG. 12b. The apparent thickness $e'_1$ of the first prism 131 and the apparent thickness $e'_2$ of the second prism 132 are decreased with respect of the apparent thicknesses $e_1$ and $e_2$ of the first configuration of FIG. 12a. In the second configuration, the pair of prisms is equivalent to an optical plate with a thickness of e'1+e'2, which is thinner than previously. It is therefore possible to have a configurable optical curvature compensator equivalent to an optical plate with a configurable thickness. In these examples, reference is made to an optical axis. Such an optical axis is the optical axis of the arm where the optical curvature compensator is arranged. Since the optical path in an arm is parallel to the optical axis, any indication given with respect to the optical axis can be understood as an indication given with respect to the optical path inside said arm.

In order to adapt the optical curvature compensator to the desired transverse variation distribution profile of the optical path length, the FFOCT can comprise a control loop to find the suitable optical path length modification profile. The control loop aims at maximizing the useful field of view. The control loop is based on an analysis of a bidimensional image acquired by the imager 114, from which is derived a command of an actuator commanding the optical curvature compensator. The control loop therefore comprises suitable components to do so, such as a processor. The analysis for example aims at localizing where the signal is present and where the signal is absent. For example, the acquired image can be divided in a number of zones (for example 5 to 20 zones) distributed over the surface of the acquired image. The zones can simply be squares or rectangles. In each zone, the pixel values (e.g. grayscale values) of all the pixels of said zone are summed. Through a comparison of the resulting sum with a predetermined threshold, each zone can be classified as a "good" region where the signal is present because coherence gates coincide and a "bad" region where the signal is absent because coherence gates do not coincide. The configurable optical curvature compensator is then modified in a way that would turn the bad regions into good regions. The control loop can also be used to choose among a set of invariant optical curvature compensators.

Accordingly, the method can comprise acquiring a first bidimensional en face FFOCT image of the layer of interest 115, and then a second bidimensional en face FFOCT image of the layer of interest 115 with an improved compensation of the curved profile of transverse variation distribution of the first optical path length. From the first bidimensional en face FFOCT image, it is determined whether the curved profile of transverse variation distribution of the first optical path length has been compensated by the optical compensator. As explained above, such a determination can for example rely on the density of visible interference fringes, or rely on the shape of the imaged field (ring shapes) and/or the signal level. If it is determined that the curved profile of the transverse variation distribution of the first optical path length was not compensated by the optical compensator, for example because the fringe density is too high, the optical compensator is modified to better compensate the curved profile of transverse variation distribution of the first optical path length. Then a second bidimensional en face FFOCT image of the layer of interest 115 is acquired with the imager 114 from reference light and sample light combined in the beam splitter 103. Since the modification of the optical compensator aims to improve the compensation, the criterion used to assess said compensation must also show improvement with respect to the first image. For example, the fringe density is reduced. If the result is still unsatisfactory, the optical compensator is modified can again be modified to better compensate the curved profile of transverse variation distribution of the first optical path length, and other images can be acquired, until the compensation of the curved profile of transverse variation distribution of the first optical path length meets the expectations.

Figure 2C:
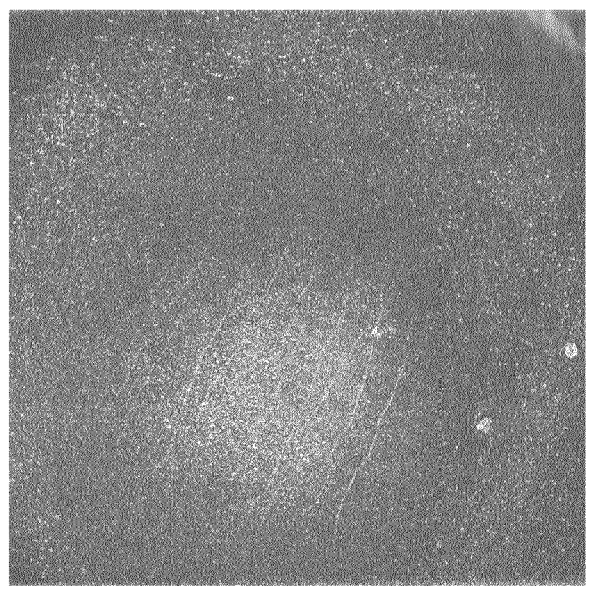
Figure 3A:
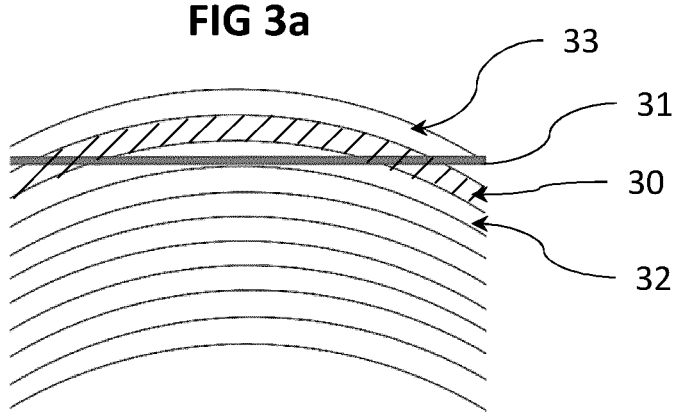
FIGS. 3a, 3b, 3c, 3d illustrate how the field of view may come as a ring-shape when a curved layer of interest is imaged through an interfering flat plane.
Figure 3B:
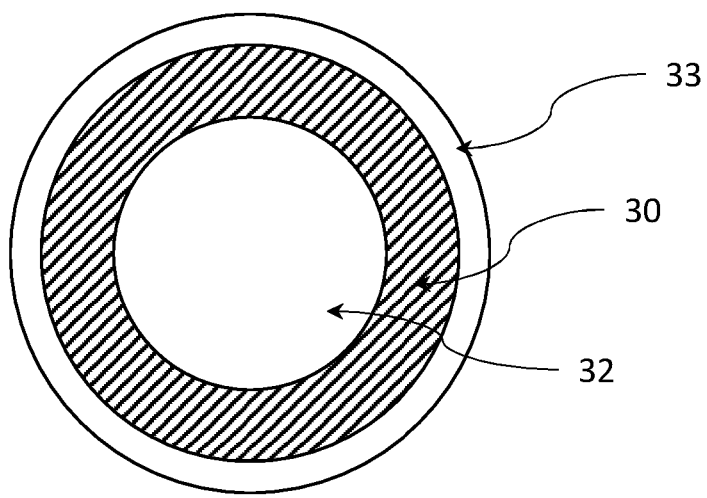
Figure 3C:
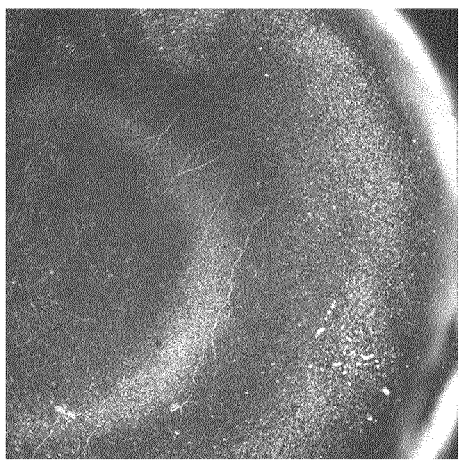
Figure 3D:
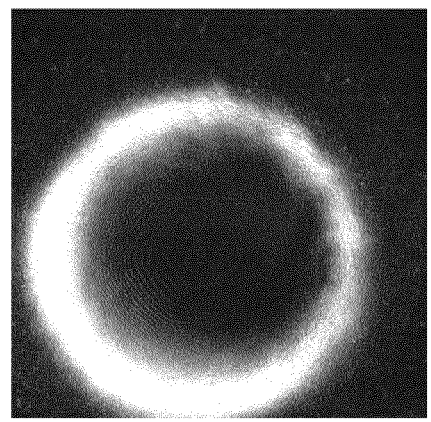

In the example of FIG. 2c, the bad regions correspond to the peripheral zones of the acquired image, which means that the coherence gates coincide only at the centre, as schematized in FIG. 2a. In the example of FIG. 3c, the bad regions correspond to the central zones of the acquired image, which means that the coherence gates coincide only at the periphery, as schematized in FIG. 3a. A command is generated to curve the transverse variation distribution profile of the optical path length of the arm in which the optical curvature compensator is arranged, so that the reference optical path length travelled by the reference light incident on the imager 114 and the second optical path length travelled by the interest light incident on the imager 114 have the same transverse variation distribution profile. For example, if the optical curvature compensator is a deformable curved mirror 112 in the reference arm 108, the command will be applied to the actuators that control the curvature of the deformable curved mirror 112 to increase the curvature. If the optical curvature compensator is a pair of prisms, the command will be applied to the actuators controlling the transverse translations of the prisms. If the pair of prisms is arranged within the reference arm 108, the prisms will be translated to increase the apparent thickness of material, in order to further curve the transverse variation distribution profile of the reference optical path length. If the pair of prisms is arranged within the sample arm 108, the prisms will be translated to decrease the apparent thickness of material, to decrease the curvature of the transverse variation distribution profile of the sample optical path length.

Figure 13A:
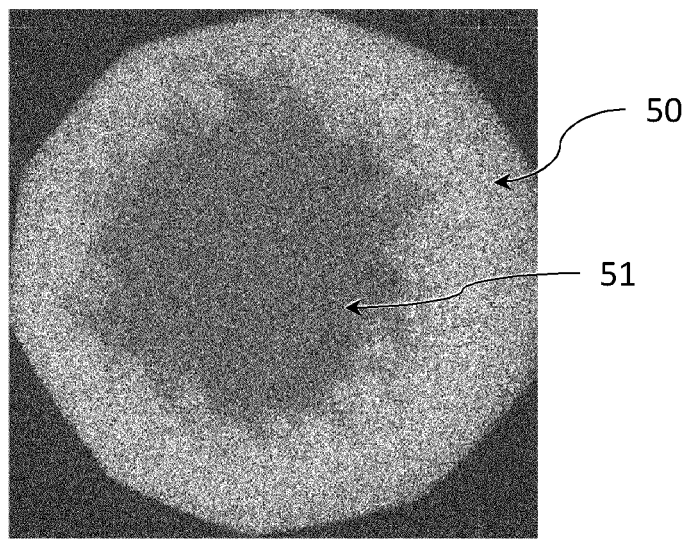
FIGS. 13a and 13b show results of the full-field imaging of a retinal layer, without and with an optical curvature compensation according to a possible embodiment of the invention, respectively.
Figure 13B:
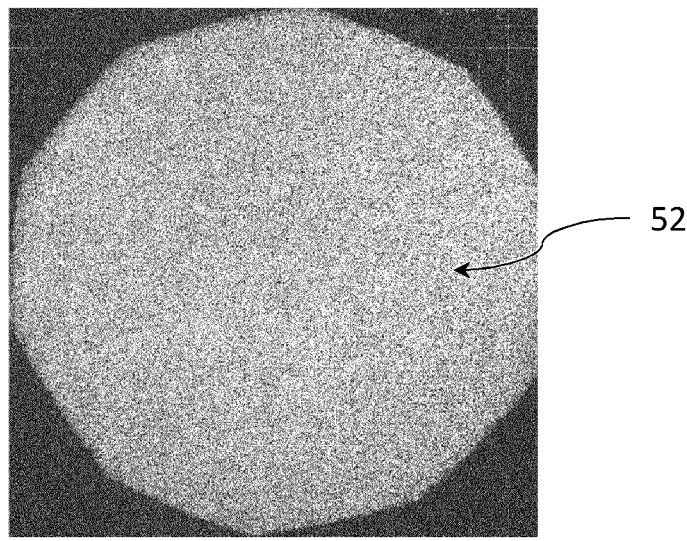

FIG. 13a shows an actual FFOCT image resulting from the imaging of a retinal layer of an artificial eye, without optical curvature compensation as disclosed above. The result is a ring shape 50 of the retinal layer to be imaged, the central portion 51 corresponding to an overlaying layer. There is no match between the transverse variation distributions of the optical path lengths travelled by the reference light and the interest light incident on the imager 114. This corresponds to the situation illustrated by FIGS. 3a-3d. FIG. 13b shows an actual FFOCT image resulting from the imaging of the retinal layer of an artificial eye as FIG. 13a, this time by performing a method as disclosed above, wherein an optical curvature compensator modifies a transverse variation distribution of an optical path length to match the transverse variation distributions of the optical path lengths travelled by the reference light and the interest light incident on the imager. On this image, it can be seen that the imager 114 has imaged the layer of interest over the whole field of view 52 of the imager 114. This means that the interest light originating from the layer of interest has interfered with the reference light over the whole field of view 52 of the imager 114. The method therefore allows imaging a layer of interest over a whole and continuous field of view.

Figure 14A:
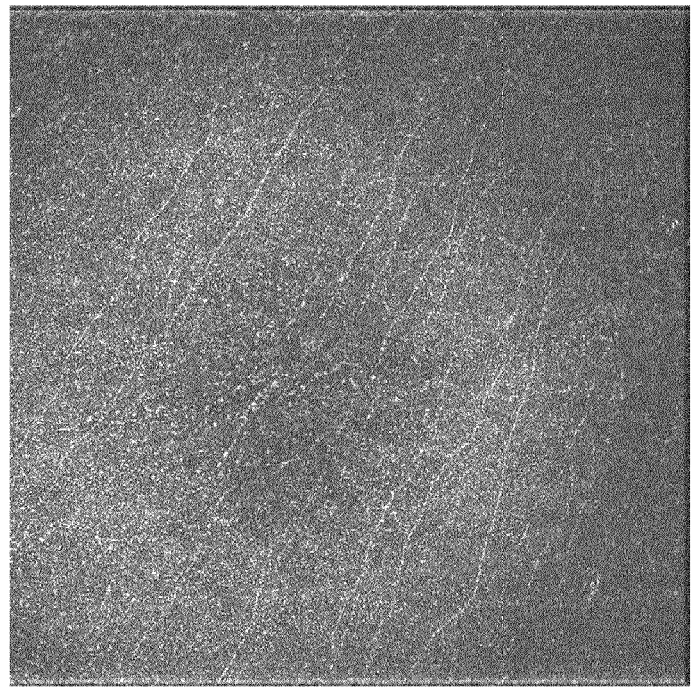
FIGS. 14a and 14b show actual final FFOCT image resulting from the imaging of the sub-basal nerve plexus and of the corneal endothelium layer, respectively, with optical curvature compensation according to possible embodiments of the invention.
Figure 14B:
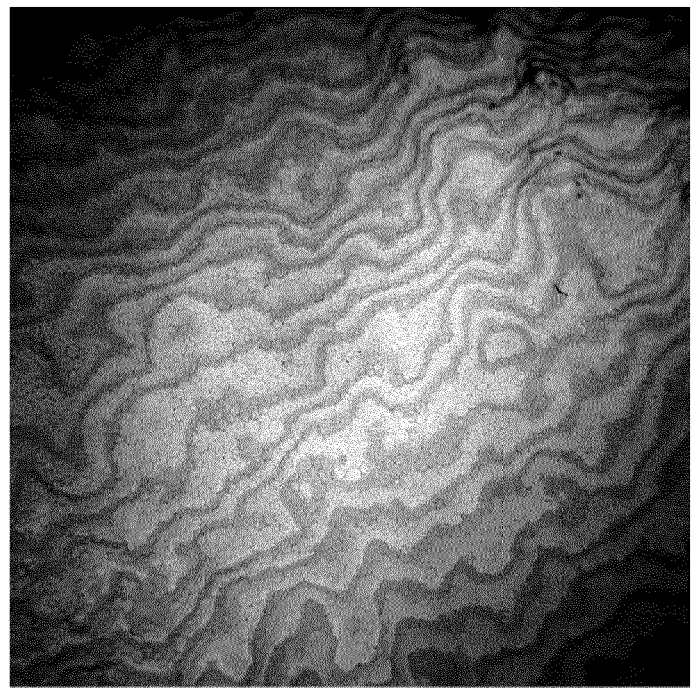

FIG. 14a shows an actual final FFOCT image resulting from the imaging of the sub-basal nerve plexus, as FIG. 3c, but this time by performing a method as disclosed above, with an optical curvature compensation. Compared with FIG. 3c where the imaged sub-basal nerve plexus in the anterior cornea appeared as a ring in the final image, the sub-basal nerve plexus of the anterior cornea is no more ring-shaped, but instead occupies the whole field of view. FIG. 14b shows an actual FFOCT image resulting from the imaging of the corneal endothelium layer as FIG. 3d, but this time by performing a method as disclosed above with an optical curvature compensation. Compared with FIG. 3d where the imaged the corneal endothelium layer in the posterior cornea appeared as a ring in the final image, the endothelium layer of the posterior cornea is no more ring-shaped, but instead occupies the whole field of view. It can thus be seen that the disclosed method allows imaging each of the layer over the whole a field of view of the imager 114.

Although the present invention has been described with respect to certain preferred embodiments, it is obvious that it is in no way limited thereto and it comprises all the technical equivalents of the means described and their combinations. In particular, it will be apparent to those skilled in the art that various changes and modifications may be made without departing from the scope of the invention as defined in the appended claims.

The invention claimed is:

1. An imaging method,
the method performing a full-field optical coherence tomography imaging, FFOCT,
the method comprising acquiring a bidimensional en face FFOCT image of a layer of interest at a depth within a sample,
the method using a system comprising a FFOCT device,
the sample comprising the layer of interest that is to be imaged,
the FFOCT device comprising:
  a spatially incoherent light source,
  an imager,
  a beam splitter defining a sample arm and a reference arm, the sample being arranged at an extremity of the sample arm,
wherein the method comprises:
  simultaneously illuminating the sample arm and the reference arm at an illumination instant with an illuminating light emitted by the incoherent light source to generate sample light travelling from the sample into the extremity of the sample arm along a sample optical path and reference light traveling in the reference arm to the beam splitter along a reference optical path,
  acquiring a bidimensional en face FFOCT image of the layer of interest with the imager from reference light and sample light combined in the beam splitter;
wherein the sample light contains interest light derived from the illuminating light emitted at the illumination instant and originating from the layer of interest of the sample, the interest light having travelled a first optical path length when entering the sample arm, the first optical path length having a curved profile of transverse variation distribution,
wherein reference light incident on the imager has travelled a reference optical path length along the reference optical path, and interest light incident on the imager has travelled a second optical path length,
wherein the reference arm comprises an optical curvature compensator that modifies a transverse variation distribution of the reference optical path length travelled by the reference light incident on the imager to compensate the curved profile of transverse variation distribution of the first optical path length, so that the transverse variation distribution of the reference optical path length travelled by the reference light incident on the imager and the transverse variation distribution of the first optical path length travelled by the interest light incident on the imager coincide, resulting in the interest light originating from the layer of interest interfering with the reference light and the imager imaging the layer of interest over a field of view of the imager to form the bidimensional en face FFOCT image acquired by the imager,
wherein the optical curvature compensator is a curved reflector having a curved reflecting surface, the curved reflector arranged at an end of the reference arm opposed to the beam splitter.

2. The method of claim 1, wherein a curved profile of the transverse variation distribution of the first optical path length has an absolute radius of curvature comprised between 4 and 50 millimetres.

3. The method of claim 1, wherein the transverse variation distribution of the reference optical path length travelled by the reference light incident on the imager and the transverse variation distribution of the second optical path length travelled by the interest light incident on the imager have a difference of absolute radius of curvature below 2 millimetres.

4. The method of claim 1, wherein the reflector has a reflectance below 25%.

5. The method of claim 1, wherein the curved reflecting surface of reflector is an optical lens.

6. The method of claim 1, wherein the curved reflecting surface of reflector is a deformable mirror.

7. The method of claim 1, wherein the optical curvature compensator is a plate of material having a refractive index and a thickness in the direction of the reference optical path or the sample optical path.

8. The method of claim 1, wherein the optical curvature compensator is a configurable optical curvature compensator, and the FFOCT device comprises a control loop configured to analyse an acquired image and derive a command to change a configuration of an optical curvature compensator, each configuration defining a different modification of the transverse variation distribution of an optical path length.

9. The method of claim 1, comprising:
acquiring a first bidimensional en face FFOCT image of the layer of interest with the imager from reference light and sample light combined in the beam splitter;
determining whether the curved profile of transverse variation distribution of the first optical path length has been compensated by the optical compensator;
if the curved profile of the transverse variation distribution of the first optical path length is determined as not compensated by the optical compensator, modifying the optical compensator to compensate the curved profile of transverse variation distribution of the first optical path length so that; and
acquiring a second bidimensional en face FFOCT image of the layer of interest with the imager from reference light and sample light combined in the beam splitter.

10. A full-field optical coherence tomography, FFOCT, device comprising:
a spatially incoherent light source configured to emit an illuminating light at an illumination instant,
an imager configured to acquire a bidimensional en face FFOCT image of a layer of interest,
a beam splitter defining a sample arm and a reference arm, the sample containing the layer of interest at a depth within the sample and being arranged at an extremity of the sample arm,
wherein at least one of the sample arm and the reference arm comprises an optical curvature compensator configured to modify a transverse variation distribution of an optical path length to compensate a curved profile of transverse variation distribution of the first optical path length travelled by an interest light derived from the illuminating light emitted at the illumination instant and originating from the layer of interest of the sample when the interest light enters the sample arm, and
wherein the FFOCT device is configured to perform the method of claim 1 to acquire a bidimensional en face FFOCT image of the layer of interest at a depth within the sample.

11. An imaging method,
the method performing a full-field optical coherence tomography imaging, FFOCT,
the method comprising acquiring a bidimensional en face FFOCT image of a layer of interest at a depth within a sample,
the method using a system comprising a FFOCT device,
the sample comprising the layer of interest that is to be imaged,
the FFOCT device comprising:
a spatially incoherent light source,
an imager,
a beam splitter defining a sample arm and a reference arm, the sample being arranged at an extremity of the sample arm,
wherein the method comprises:
simultaneously illuminating the sample arm and the reference arm at an illumination instant with an illuminating light emitted by the incoherent light source to generate sample light travelling from the sample into the extremity of the sample arm along a sample optical path and reference light traveling in the reference arm to the beam splitter along a reference optical path,
acquiring a bidimensional en face FFOCT image of the layer of interest with the imager from reference light and sample light combined in the beam splitter;
wherein the sample light contains interest light derived from the illuminating light emitted at the illumination instant and originating from the layer of interest of the sample, the interest light having travelled a first optical path length when entering the sample arm, the first optical path length having a curved profile of transverse variation distribution,
wherein reference light incident on the imager has travelled a reference optical path length along the reference optical path, and interest light incident on the imager has travelled a second optical path length,
wherein at least one of the sample arm and the reference arm comprises an optical curvature compensator that modifies a transverse variation distribution of an optical path length to compensate the curved profile of transverse variation distribution of the first optical path length, so that the transverse variation distribution of the reference optical path length travelled by the reference light incident on the imager and the transverse variation distribution of the second optical path length travelled by the interest light incident on the imager coincide, resulting in the interest light originating from the layer of interest interfering with the reference light and the imager imaging the layer of interest over a field of view of the imager to form the bidimensional en face FFOCT image acquired by the imager, wherein the optical curvature compensator comprises a pair of prisms, each prism having an inclined surface forming a non-right inclination angle with respect to the optical path, the non-right inclination angles of the pair of prisms being opposite with each other, the prims being movable in translation one with respect to one another.

* * * * *